United States Patent [19]

DenBeste et al.

[11] Patent Number: 4,992,267

[45] Date of Patent: Feb. 12, 1991

[54] HAIR STRAIGHTENING COMPOSITION AND SYSTEM

[75] Inventors: Marion DenBeste, Arlington Heights; Muhammad Akhtar, Bolingbrook, both of Ill.

[73] Assignee: Johnson Products Co., Inc., Chicago, Ill.

[21] Appl. No.: 187,605

[22] Filed: Apr. 28, 1988

[51] Int. Cl.$^5$ .......................... A61K 7/09; A45D 7/04
[52] U.S. Cl. ......................................... 424/71; 424/72; 132/203
[58] Field of Search ..................... 424/71, 72; 132/202, 132/203, 209

[56] References Cited

U.S. PATENT DOCUMENTS

| | | | |
|---|---|---|---|
| 3,017,328 | 1/1962 | Childrey | 167/87.1 |
| 3,242,052 | 3/1966 | Sheffner | 167/87.1 |
| 3,243,346 | 3/1966 | Beckmann et al. | 167/87 |
| 3,252,866 | 5/1966 | Sheffner | 167/87.1 |
| 3,533,417 | 10/1970 | Twickenham | 132/7 |
| 3,908,672 | 9/1975 | Bore et al. | 132/7 |
| 3,971,391 | 7/1976 | Bore et al. | 132/7 |
| 4,139,610 | 2/1979 | Miyazaki et al. | 424/72 |
| 4,153,681 | 5/1979 | Shiba | 424/72 |
| 4,175,572 | 11/1979 | Hsiung et al. | 132/7 |
| 4,218,435 | 8/1980 | Shiba | 424/72 |
| 4,272,517 | 6/1981 | Yoneda et al. | 424/72 |
| 4,322,401 | 3/1982 | Harada | 424/72 |
| 4,327,910 | 12/1980 | Khalil et al. | 132/7 |
| 4,361,157 | 11/1982 | James | 132/7 |
| 4,390,033 | 6/1983 | Khalil et al. | 132/7 |
| 4,424,820 | 1/1984 | Cannell et al. | 132/7 |

FOREIGN PATENT DOCUMENTS 1002889 9/1965 United Kingdom .

OTHER PUBLICATIONS (Hereld letter to editor), "Cysteine Wave Lotions", *Cosmet. Toilet.*, 103, 7 (1988).

"Cysteine and Cysteine Derivatives in Skin—and Hair–Care Agents" (undated), technical bulletin published by Diamalt/Pharmazell Aktiengesellschaft.

*Primary Examiner*—Merrell C. Cashion, Jr.
*Assistant Examiner*—Susan S. Rucker
*Attorney, Agent, or Firm*—Olson & Hierl

[57] ABSTRACT

An improved no-base aqueous sodium hydroxide-based hair-straightening composition having a pH between about 12 and about 14 comprises, as an active hair-straightening agent, a mixture of sodium hydroxide and a lesser amount of a hair keratin-disulfide reducing agent having a sulfhydryl functional group available from the sulfur-containing amino acid cysteine, water-soluble homologs of cysteine and certain water-soluble derivatives of cysteine. The composition augments and enhances the hair-straightening benefits of sodium hydroxide yet substantially overcomes negative hair conditioning problems normally associated with the use of sodium hydroxide. Cysteine is particularly preferred as the hair keratin-disulfide reducing agent. Also disclosed is a hair-straightening system and method for straightening hair with the foregoing compositions.

27 Claims, No Drawings

HAIR STRAIGHTENING COMPOSITION AND SYSTEM

TECHNICAL FIELD

This invention relates to the straightening or relaxing of hair, and in particular to sodium hydroxide-based hair straightening compositions having improved hair condition benefits.

BACKGROUND ART

Hair straightening or relaxing has become increasingly popular in view of hair styles which require relatively or perfectly straight hair. Several types of hair straightening products are available, but sodium hydroxide is generally judged the most effective agent for substantially permanently straightening kinky-curly negroid hair. Until now, however, relatively high concentrations of greater than about 2.5 weight percent sodium hydroxide were required resulting in decreased hair condition benefits and increased skin irritation.

Hair straightening or relaxer products most commonly used in salons and in the home contain as the sole active hair-straightening agent, either a strong alkali, such as sodium hydroxide or guanidine hydroxide; a sulfite, typically an ammoniacal mixture of bisulfite and sulfite; or a thiol compound, typically ammonium thioglycolate. All of these types of products exert their primary reducing effect by breaking the cystine disulfide bonds present in hair keratin, referred to as hair keratin-disulfide bonds. The chemical action of alkali-based straightening, sulfite-based straightening and thiol-based straightening is known to differ to varying extents, with alkali, especially, producing additional stable crosslinks in the hair that are not normally present in virgin hair.

The majority of hair-straightening kits sold for home use are based on the sulfite or thioglycolate straighteners. However, these have several inherent disadvantages. One major disadvantage is the highly offensive odor of the thioglycolate solutions and of the thiol-reduced hair. Another disadvantage is that thiol-based straightening requires the use of an oxidizing neutralizer, such as hydrogen peroxide, to chemically relink the hair keratin-disulfide bonds and stop the straightening process quickly. Since the thiol-reduced hair is in an alkaline state, any excess neutralizer must also be removed to avoid bleaching the natural color of the hair. Sulfite-based straighteners have similar disadvantages. For example, sulfite-containing solutions can deteriorate gradually and release offensive odors of sulfur dioxide. Sulfite-reduced hair also must be neutralized by bringing the hair to an alkaline pH to reverse the keratin-sulfite reaction and chemically re-link the hair keratin-disulfide bonds.

On the other hand, strong alkalis, such as sodium hydroxide and guanidine hydroxide, have several advantages over the sulfite or thioglycolate agents. These alkalis do not have a highly objectionable odor or cause such an odor on reducing the hair. Alkali-straightened hair is treated at a highly alkaline pH of between about 12 and about 14. At that alkalinity, alkalis are known to form stable irreversible cross-links of lanthionine and lysinolanine in the reduced hair making a chemical relinking step unnecessary. Thus, the only step required following an alkali-based straightening process is to remove substantially all excess alkaline solution to avoid and minimize damage to the hair protein or skin. For this purpose, an acidic shampoo is usually used to neutralize residual alkali on and remove it from the hair and scalp. Guanidine hydroxide, unlike sodium hydroxide, is not chemically stable in solution for any practical storage period. Consequently, it must be freshly prepared prior to using (usually within 24 hours). For this reason, guanidine hydroxide-based straighteners are supplied as a two-component package. Thus, despite its causticity, sodium hydroxide-based hair straightening or relaxer kits, which became available around 1958, are still popular and widely used in professional shops. The sodium hydroxide-based relaxer has also continuously gained popularity for home use since its introduction to the retail market in 1971.

The main advantages of a sodium hydroxide straightener are relatively fast processing times and good straightening of naturally kinky-curly negroid hair. Additionally, the straightening effect is more permanent; i.e., less likely to revert to a curly state after shampooing and wearing than is hair straightened with other straighteners.

The principal disadvantages of sodium hydroxide-based hair straighteners, of course, is their causticity which can adversely affect hair condition, leaving it in a brittle state and harsh to the touch. Additionally, prolonged or unnecessary exposure of hair to strong alkali at about pH 12 or above can weaken, break and dissolve the hair. In some instances, strong alkali discolors the natural color of the hair. For example, the tone of natural brown hair is reddened and natural white or grey hair is undesirably yellowed and brightness is dulled. Thus, another disadvantage is delustering of the natural sheen of the hair.

The concentration of sodium hydroxide used for modern hair-straightening procedures can vary between about 1.5 to about 3.5 weight percent, depending on whether the product is a "base" or "no-base" relaxer. The terms "base relaxer" mean that the scalp and hair line must be coated with a protective oleaginous base, such as petrolatum, mineral oil and lanolin, before applying the hair relaxer. The terms "no-base relaxer" means that the scalp need not be coated with a protective base. In some cases, where the no-base hair relaxer incorporates sodium hydroxide in an oleaginous cream base, protective base frequently need only be applied to the hairline to protect the skin around the forehead, ears and neckline. No-base relaxer processes, therefore, are preferred.

Some past attempts have been made to use chemical straighteners, other than sodium hydroxide, sulfite and thioglycolates, such as mercapto-substituted compounds and various combinations of chemical treatments and heat. A discussion of these studies can be found in the books by deNavarre, *The Chemistry and Manufacture of Cosmetics*, Second Edition, Vol. IV, Continental Press, Orlando, Fla. (1975), and by Sagarin, *Cosmetics: Science and Technology*, Second Edition, Vol. 2, Wiley-Interscience, New York, N.Y. (1972). The disclosure of both of these books are incorporated herein by reference. A review of other chemical hair straighteners and waving agents reported in the patent literature also can be found in *Cosmetics & Toiletries*, 94, 61–69 (April) 1979 and 100, 23–29 (April) 1985, also incorporated herein by reference. These attempts have met with varying degrees of success. But, except for possibly guanidine hydroxide, other chemical hair-straightening agents have not achieved any substantial measure of practical or commercial importance in the hair-straightening arts beyond scientific interest.

In cold hair waving arts, which by analogy extends to hair-straightening arts, some interest and success has been reported most recently from the use of the sulfur-containing amino acid, cysteine, its mineral acid salts, especially cysteine hydrochloride, and certain cysteine derivatives, such as N-acetyl-L-cysteine. Cysteine and cysteine-derived compounds are of cosmetic interest, because they are water-soluble, substantially odorless and acceptable for use in cold-wave processes as a hair keratin-disulfide reducing agent. The terms "cold-wave process" are used in the conventional sense to mean that permanent hair waving or straightening is achieved at between ambient room temperature and body temperature, usually at about 30 degrees C. (about 86 degrees F.) without the assistance of externally applied heat.

Cysteine, however, used as a main hair-straightening agent has certain disadvantages. For example, relatively high amounts of upwards of about 3 weight percent to about 20 weight percent of cysteine (or a cysteine derivative) are reportedly required to effect a beneficial change in the configuration of the hair. Like other sulfhydryl compounds, cysteine acts on the cystine disulfide bonds in hair keratin, so the treated hair must be chemically neutralized to re-link the hair keratin-disulfide bonds. In addition, cysteine oxidizes readily to insoluble cystine which can deposit as crystals on the skin and form a dulling film on the hair.

The reported useful pH of various compositions containing cysteine or cysteine derivatives in the literature generally ranges between about pH 6 to about pH 11. However, to minimize skin irritation and maximize the action of the cysteine or its derivatives on hair, a pH of about 10 or less is usually required. Sodium hydroxide has been disclosed as a cosmetically acceptable inorganic base to adjust the alkalinity of some of the foregoing compositions reported in the literature. However, volatile ammonium hydroxide and organic amine bases are generally prepared, and the amount of sodium hydroxide, if used, to adjust the pH is rather miniscule. For example, it is known that a solution of sodium hydroxide at 0.05 weight percent has a pH of 12. Thus, even if some sodium hydroxide were available as free base at a pH of about 11, the amount present would be too low to straighten hair. It is also known that sodium hydroxide at below about pH 12 and at a titratable alkalinity of less than about 0.5 weight percent effects substantially no straightening of curly hair. Thus, cysteine and other water-soluble cysteine derived compounds have not provided a viable alternative to sodium hydroxide-based hair-straightening.

Some strides have been made in improving the conditon of sodium hydroxide-straightened hair by incorporating conditioners into the alkaline product. See, for example, U.S. Pat. No. 4,175,572, which issued to our assignee and which is incorporated herein by reference. However, there is still a need for a sodium hydroxide-based hair straightening composition having relatively low concentrations of sodium hydroxide for use in a no-base relaxer process, yet retaining beneficial hair straightening effects equivalent to or better than those obtained from higher amounts presently used. An ideal sodium hydroxide-based hair straightening composition, system and method would also provide a relatively fast processing time and good hair condition.

The hair straightening compositions, system and method of this invention provide a solution to this longstanding need by providing an improved sodium hydroxide-based hair straightener containing an auxiliary hair-straightening agent in which many of the above drawbacks are overcome. In addition, the auxiliary hair-straightening agent is a polar hair keratin-disulfide reducing agent having an active sulfhydryl functional group available from the sulfur-containing amino acid, cysteine and cysteine-derived compounds. Thus, good hair-straightening benefits are retained and good hair condition is obtained.

SUMMARY OF THE INVENTION

This invention relates to an improved no-base aqueous sodium hydroxide-based hair-straightening composition (referred to as a hair-straightener for convenience) having a pH of between about 12 and 14. In particular, the present hair-straightener comprises a mixture of at least two active hair-straightening agents; namely sodium hydroxide as a main hair-straightening agent and an auxiliary hair-straightening agent. More particularly, the hair-straightening agents comprise a mixture of sodium hydroxide and a lesser amount of a hair keratin-disulfide reducing agent having a sulfhydryl functional group available from the sulfur-containing amino acid cysteine, water-soluble homologs of cysteine and water-soluble derivatives of cysteine having none, one or both of its polar amino, and carboxy acid group substituted. Cysteine base is particularly preferred.

In one surprising aspect, the effectiveness of sodium hydroxide as a straightener was augmented by including cysteine base as an auxiliary hair-straightening agent while retaining good hair condition. In another aspect, the improved hair-straightener of this invention enhanced the straightening effect obtained with a relatively low concentration of sodium hydroxide to a level approximating or substantially equivalent to that obtained with the higher amounts used in commercial so-called Super-strength sodium hydroxide-based products. In addition, enhanced straightening was achieved in a substantially shortened process time.

The term "relatively low" refers to sodium hydroxide at concentrations of between about 1 weight percent to about 2.2 weight percent, preferably between about 1.5 and about 2 weight percent based on the total weight of the hair straightener when it is applied to the hair. A commercially practical amount of sodium hydroxide for sodium hydroxide-based hair straighteners can be up to about 2.5 weight percent for use on coarse and tightly curled/kinky hair that is generally resistant to straightening. While it is recognized that higher amounts of sodium hydroxide can be used, these are not desirable owing to the increase in skin problems and decrease in hair condition they present. The term "hair condition" encompasses the objectively measurable character of hair, such as tensile strength, the subjectively perceptible character, such as natural color and its tonal quality, natural luster or sheen, and odor, as well as tactile properties, such as smoothness, silkiness, softness and other like properties similarly determined by feel.

An improved no-base hair-straightening composition of this invention, therefore, comprises a mixture of sodium hydroxide at about 1 to about 2.5 weight percent and an auxiliary hair-straightening agent at about 0.1 to about 1.5 weight percent based on the total weight of the hair-straightener applied to the hair. A particularly preferred hair straightener having a pH of between about 12.5 to about 13.5 comprises a mixture of sodium hydroxide at about 1.5 to about 2.2 weight percent and cysteine at about 0.25 to about 1 weight percent based on the total weight of the hair-straightener.

In the improved no-base hair-straightening systems of this invention, the auxiliary hair-straightening agent can be included as an ingredient along with the sodium hydroxide in a single package supplied for use directly as the hair straightener. Alternatively, the auxiliary hair-straightening agent can be packaged separately and admixed with an aqueous composition containing the sodium hydroxide hair-straightening agent prior to use. In that instance, the hair-straightening system comprises at least two packages; the contents of one containing the sodium hydroxide, and the contents of the second containing the auxiliary hair-straightening agent. When the contents of the first package and second package are mixed, a hair-straightener is provided.

A hair-straightener of this invention has several benefits and advantages. A main benefit is that the straightening effect usually obtained with relatively low concentrations of sodium hydroxide hair straighteners can be enhanced to a level approximating or equivalent to that obtained with high concentrations without increasing the attendant problems.

Another benefit is that the natural color of the pre-straightened hair is substantially retained after straightening by practicing the principles of this invention, thereby overcoming discoloration problems normally associated with highly alkaline hair straightening. Still another benefit is that skin irritation problems normally associated with the relatively high concentration of sodium hydroxide usually required for straightening effects that are equivalent to those obtained with compositions of this invention are avoided.

In addition, by using the auxiliary hair-straightening agents of this invention, less sodium hydroxide can be used in commercial sodium hydroxide-based hair-straighteners without sacrificing effectiveness and at the same time gaining improved hair condition.

Still further advantages and benefits will be apparent to those skilled in the art from the description, examples and claims which follow.

DETAILED DESCRIPTION OF THE INVENTION

It has now been found that aqueous no-base sodium hydroxide-based hair-straighteners having a pH between about 12 and about 14 can be improved by augmenting or enhancing the straightening action of sodium hydroxide while improving hair condition. This improvement, which particularly enhances relatively low amounts of sodium hydroxide that would otherwise provide only marginal or mild hair-straightening, results from the inclusion of relatively low amounts of an auxiliary hair keratin-sulfide reducing agent having a sulfhydryl functional group available from cysteine, homologs of cysteine, and water-soluble derivatives of cysteine having none, one or both of the polar amino and carboxy acid groups substituted.

With reference to sodium hydroxide, the term "relatively low amount" refers to a titratable alkalinity of between about 1 to about 2.2 weight percent sodium hydroxide based on the total weight of the hair-straightening composition when it is applied to the hair. In the United States, sodium hydroxide is typically provided at a titratable alkalinity of between about 2 to about 2.2 weight percent in hair-straighteners generally classified as "Mild-strength" and "Regular-strength" in commercial practice. These hair-straightening compositions are generally useful for fine textured hair having only a loose to moderately tight curl pattern.

For straightening coarse and very curly/kinky afro or negroid hair, however, Super-strength hair-straightening compositions having a higher amount of sodium hydroxide are required. Some commercial Super-strength hair straightening compositions can have up to about 3.5 weight percent sodium hydroxide or more. However, as the concentration of sodium hydroxide increases so does the potential for problems relating to skin irritation and hair damage from increased causticity.

For practicing the principles of this invention, therefore, sodium hydroxide can be at between about 1 weight percent to about 2.5 weight percent, preferably between about 1.5 weight percent to about 2.2 weight percent and more preferably between about 1.75 weight percent to about 2 weight percent. Weight percent refers throughout to the weight of a component based on the total weight of the hair-straightener when it is applied to the hair.

With reference to the disclosed auxiliary hair-straightening agent of this invention, the term "relatively low amount" refers to a concentration of between about 0.1 weight percent to about 1.5 weight percent, preferably between about 0.25 and about 1 weight percent and more preferably between about 0.5 to about 0.75 weight percent.

Cysteine is a sulfur-containing amino acid having an available polar sulfhydryl functional group as well along with polar amino and carboxy acid groups. In the free base form, also called cysteine base, the structural formula is $HSCH_2CH(NH_2)COOH$ which has a reported dissociation constant (pK) of $pK_1$ 1.71; $pK_2$ 8.33; and $pK_3$ 10.78. Thus, cysteine base is particularly preferred because the polar sulfhydryl functional group is directly available and ionizable at a highly alkaline pH of between about 12 and about 14. Reference to cysteine herein is to cysteine base.

For the practice of this invention, cysteine can be selected from either its D-form, L-form, DL-form or mixtures thereof. In addition, cysteine is substantially odorless, readily water-soluble, generally considered substantially innocuous for use on human skin, and is commercially available from various chemical suppliers. Cysteine will be used, therefore, for purposes of discussing, describing, and illustrating the principles of this invention, but not by way of limitation as discussed below.

Cysteine at less than about 3 weight percent is not normally useful for either straightening or waving hair. Surprisingly, when relatively low amounts of cysteine were included in a sodium hydroxide-based hair-straightening composition (hereafter improved hair-straightener), the straightening effect normally achieved, especially with a relatively low amount of sodium hydroxide was noticeably augmented. For example, the straightening effect on hair with an improved commercial Mild-strength composition was enhanced to a level substantially equivalent to or approaching that usually obtained with a commercial Super-strength composition.

The cysteine also augmented the speed of the chemical action on the hair so that perceptible and enhanced straightening was reached in a shorter process time. For example, in one embodiment, the straightening effect obtained within a 13-minute processing time using an improved Regular-strength hair-straightener containing 0.75 weight percent cysteine was comparable to that usually achieved within an 18-minute processing time with the unaugmented counterpart of the same Regular-strength composition, based on an actual comparative salon test.

Also surprisingly, when improved hair-straightening compositions were prepared and used, the formation of insoluble crystal deposits of oxidized cysteine, i.e., cystine, was not observed either on the hair, the skin or in solution. This problem is normally reported for other cysteine systems.

More surprisingly, after the initial augmented boost in chemical straightening action, further chemical action was substantially stopped by the water rinsing step. Thus, substantially no post-rinsing chemical action was observed attributable to residual sulfhydryl or mercaptan compound in the hair, based on tensile fiber properties measured using an intermittent modulus technique described below. In addition, hair condition was improved.

The term "hair condition" as used herein includes the subjective properties of hair such as luster, color, and desirable tactile properties as well as tensile fiber properties reflected as fiber breakage and visibly straighter curl pattern. The terms "tensile fiber properties" includes the physical and chemical characteristics of human hair associated with intact fiber integrity that, in turn, contribute to desirable mechanical properties of good hair condition, i.e., easy combability, manageability and "soft, smooth hand feel."

Thus, it is generally recognized that hair condition is a complex concept that depends on a variety of physical attributes that are subjectively evaluated by practitioners.

One important subjectively evaluated attribute is the natural color of the hair and the brightness of its tone. Discoloration or changes in hair color following an alkali-straightening procedure can be undesirable. For example, dark hair, especially dark brown and black hair, can become reddened, faded or dulled. Particularly troublesome is yellowing of natural white (grey) hair. Another important attribute that can be subjectively seen is an undesirable delustering of the natural sheen or luster associated with the previously described discoloration of the natural color of the hair.

One of the benefits of using an improved hair-straightener of this invention is good hair condition and non-yellowing or discoloration of hair. The mechanism of this invention is not fully understood. However, it is believed that the enhanced speed of the process protects and preserves those constituents in hair, other than cystine disulfide, that can be negatively affected or degraded as a function of time of exposure to alkali, and which contribute to color and sheen.

Instrumental techniques were also employed to objectively measure the effect of augmented sodium hydroxide straightening on various tensile properties of the hair, such as strength and breakage.

One of the instrumental techniques employed measures the stress-strain modulus of hair in terms of fiber elongation and axial swelling while it is actually undergoing a chemical straightening procedure. This technique is called the intermittent modulus technique because changes in the strength of the hair under an intermittently applied additional load are measured. For this purpose, a laboratory model of an intermittent modulus device was constructed and employed.

The intermittent modulus device comprises a balance attached to a beam which controls illumination of a photocell and generates a current. Light control for the photocell is electronically regulated and current is measured on a strip chart recorder.

The instrument balance beam is attached to a test hair fiber. The hair fiber is anchored at each end by a vinyl tab and is laterally positioned. The lateral position of the fiber is controlled by a micrometer, and controls are provided on the instrument to assure exact fiber alignment. The length of the hair fiber for convenience is preferably of a gauge length of about 1.5 centimeters (about 0.6 inches) but is not so limited. A constant load is placed on the hair fiber and an additional load is applied at intermittent intervals. For example, a constant load of 0.5 grams can be applied, and additional loads of 0.5 grams can be applied at 30 second intervals.

Changes in the length of the fiber cause proportional changes in the position of the recorder pen. Fiber axial swelling is influenced and controlled by applied chemical treatments thus making it possible to assess the treatment in terms of fiber axial swelling. Axial swelling changes are magnified 200 times on the recorder chart, so that a 30-millimeter (1.2 inch) pen excursion is equivalent to 1 percent change in fiber length for a fiber of about 1.5 centimeters gauge length.

Using this technique, therefore, fiber integrity is measured in terms of both fiber strength and fiber elongation. Fiber strength is determined by the height of the vertical pen excursion. For example, the greater the chemical attack, the weaker the fiber will become and this will be reflected by a greater vertical excursion by the pen. Fiber elongation is related to straightening and is reflected by changes in the vertical starting position of the pen on the recorder chart. Thus, shortening of the fiber as it weakens is readily observable. Restoration of fiber integrity is considered a reversal of weakened fiber strength and supercontraction.

From our experience, calculated values of percent loss in tensile strength of hair that has been straightened with highly alkaline "lye" or "no-lye" relaxers obtained with the intermittent modulus technique compare favorably with those obtained by commercially available tensile testers, such as the Scott Tensile Tester, GCA/Precision Scientific, Chicago, Ill. Also in this regard, a description of the construction of a laboratory model of an analogous device used to study the performance of depilatories can be found in Elliot, "Use of a Laboratory Model to Evaluate the factors Influencing the Performance of Depilatories," *J. Soc. Cosm. Chem.*, 25, 367 (1974).

The beneficial results observed by Intermittent Modulus Technique were further corroborated by improved tensile fiber properties obtained with a Scott Tensile Tester and by subjective evaluations of hair condition as well as hair-straightening as described in the following examples.

It is recognized that other strong alkali metal hydroxides, besides sodium hydroxide, can effect hair-straightening without the assistance of heat. Exemplary alkalis are potassium hydroxide and lithium hydroxide. However, sodium hydroxide is generally preferred for commercial cosmetic applications.

Although cysteine is a particularly preferred auxiliary hair-straightening agent for practicing the principles of this invention, other cosmetically acceptable cysteine compounds having a sulfhydryl functional group available can be used. For example, water-soluble homologs of cysteine and water-soluble substituted or unsubstituted derivatives of cysteine can be used in place of cysteine, in combination with cysteine, or in combination with one another. Exemplary cysteine compounds from which a sulfhydryl functional group is directly available from cysteine having either a D-, L- or DL- configuration include:

(a) homologs of cysteine, such as homocysteine and homocysteine hydrate;

(b) N-substituted derivative of cysteine, such as N-acetyl-L-cysteine and N-carbamoylcysteine;

(c) lower N-alkanoylcysteines having up to about ten carbon atoms in the alkanoyl radical, such as N-propionylcysteine, N-butyrylcysteine, N-valerylcysteine, N-caproylcysteine and N-heptanoylcysteine;

(d) N-substituted aroylcysteines, such as N-benzoylcysteine, N-toluoylcysteine, N-(ethylbenzyl) cysteine and N-(propylbenzoyl) cysteine;

(e) amides of N-acylated cysteine, such as 2-acetamide-3-mercaptopropionamide; and (f) lower alkyl esters of cysteine having up to about 3 carbon atoms in the alkyl group, such as cysteine methyl ester, cysteine ethyl ester and cysteine propyl ester.

Similarly, cysteine compounds can be used in which the sulfhydryl functional group of cysteine is indirectly available in that it becomes available upon hydrolysis in water or at an alkaline pH. Exemplary compounds include homocysteine thiolactone, N-lower alkanoyl substituted derivatives of homocysteine thiolattone having up to about four carbon atoms in the alkanoyl group and N-aroyl substituted derivatives of homocysteine thiolactone, such as N-toluoyl homocysteine thiolactone and N-(ethyl benzyl) homocysteine thiolactone.

Descriptions of some of the foregoing compounds and their chemical properties as hair keratin-disulfide reducing agents in less alkaline compositions can be found in U.S. Pat. No. 4,272,517 (N-carbamoylcysteine in combination with cysteine at pH 8 to 10); U.S. Pat. No. 3,242,052 (N-alkanoylcysteine and N-aroylcysteine at pH from about 7 to about 9.5); U.S. Pat. No. 3,252,866 (N-acylated cysteine compounds at pH between about 7 and 9.5); and U.S. Pat. Nos. 4,153,681 and 4,218,435 (lower alkyl ester of cysteine at pH 6 to 10), the disclosures of which are incorporated herein by reference. In these foregoing compositions, however, the alkalinity of the compositions was well below that required for practicing sodium hydroxide-based straightening. It is well known that at a pH below about 12, the straightening effect of sodium hydroxide is sacrificed. The chemical action on the hair fiber then primarily consists of uptake of sodium ions that form weak salt bond linkages resulting in swelling and weakening of the hair protein substrate.

It is recognized that the foregoing listing is intended by way of example and is not limiting. Similarly, the selection of one or more of the foregoing compounds for use as the auxiliary hair-straightening agent in practicing the principles of this invention is determined by economic considerations and commercial availability.

It is also recognized that inorganic mineral acid salts of cysteine, such as cysteine hydrochloride, are also known to be an effective hair keratin-disulfide reducing agent. However, for purposes of practicing the principles of this invention, the free base form of cysteine is preferred. It is also recognized that the auxiliary hair-straightening agent of this invention can be used at amounts greater than 1.5 weight percent. However, such increased amounts were not found necessary or desirable and would increase the cost unnecessarily.

It was further found that the beneficial augmentation of sodium hydroxide obtained with cysteine was not obtained when ammonium thioglycolate was used instead in a small amount of above 0.5 weight percent.

Improved no-base aqueous sodium hydroxide-based hair-straightening compositions of this invention are preferably prepared as thickened oil-in-water emulsions, and especially as oleaginous creams. Emulsions that are water-in-oil can be used, as long as sufficient water is present to dissolve or disperse the auxiliary hair reducing agent. Techniques for preparing such emulsions and creams are well known in the art.

Thus, an improved sodium hydroxide-based hair-straightener can be prepared as a single product by combining the auxiliary hair-straightening agent and the sodium hydroxide in one package.

Alternatively, where the long-term storage stability of the auxiliary hair-straightening agent under highly alkaline conditions of between about pH 12 and about pH 14 is of concern, the auxiliary hair-straightening agent can be withheld from the composition containing the active sodium hydroxide hair-straightening agent and added just prior to use to form the hair-straightener that is applied to the hair. In this case, the hair-straightening system of this invention comprises at least two packages.

A two-package no-base hair-straightening system has several advantages. The contents of the first package can comprise an aqueous composition having a pH between about 12 and about 14, preferably between about pH 12.5 and 13.5, containing sodium hydroxide as a main hair-straightening agent. The sodium hydroxide is present in a sufficient amount to provide between about 1 and about 2.5 weight percent based on the total weight of the hair-straightener that is formed by admixing the contents of the first package with the contents of a second package that includes an auxiliary hair-straightening agent. The auxiliary hair-straightening agent comprises a hair keratin-disulfide reducing agent having a sulfhydryl functional group available from the sulfur-containing amino acid cysteine, water-soluble homologs of cysteine and water-soluble derivatives of cysteine having none, one or both of the polar amino and carboxy acid groups substituted. The auxiliary hair-straightening agent is present in an amount sufficient to form a hair-straightening composition when the contents of the second package are admixed with the contents of the first package.

Preferably, the hair straightener obtained from a two-package hair-straightening system comprises, based on the total weight of the admixture, sodium hydroxide in the first package at about 1.5 to about 2.2 weight percent and auxiliary hair-straightening agent at about 0.1 weight percent to about 1.5 weight percent, more preferably at about 0.25 to about 1 weight percent.

The contents of the second package can be in either a substantially dry powder form or in a liquid form prior to being admixed with the contents of the first package. Thus, one advantage is that a single Mild-strength hair-straightening kit can be manufactured and provided to be augmented to Regular-strength or Super-strength when needed by the addition of the auxiliary hair-straightening agent. In addition, certain cosmetic adjuvants that are known to be alkali-sensitive or alkali-unstable, such as perfume, product colorant, some surfactants, conditioners and the like, can be included as ingredients in the second package, as long as they are chemically compatible with the auxiliary hair-straightening agent.

For example, as illustrated herein, the contents of the second package can be cysteine base in crystalline form. Alternatively, the auxiliary hair-straightening agent can be dispersed in water and appropriately sealed against aerial oxidation. In this case the contents of the second package are in liquid form. In either case, the second package can contain some of the cosmetic adjuvants of the hair straightener, if desired.

In the method of this invention, the disclosed improved sodium hydroxide-based hair straightener can be applied to the hair by techniques well known in the art to at least partially straighten those portions of the hair that have received no prior chemical hair straightening treatment, i.e., substantially virgin outgrowth. It is generally well known that the length of time that the hair is exposed to a highly alkaline straightener or relaxer product varies with the amount of curl in the hair and the strength of the alkaline straightening agent. Typically, this length of time is determined by the practitioner based on the amount of partial or complete removal of natural curl desired. Less than about 20 minutes, preferably less than about 15-18 minutes, is desirable. Substantially all the hair straightener product is then removed from the hair, preferably by rinsing with water. Substantially immediately thereafter, a post-straightening shampoo is usually applied for purposes of cleansing and removing residual hair composition from the hair or scalp. Any of a number of conventional shampoos typically used by practitioners in the hair straightening arts can be employed. Typically, such shampoos are called neutralizing shampoos and have an acidic to neutral pH.

The following Examples illustrate hair straightening compositions and methods of this invention, but are not intended to be limiting.

EXAMPLE 1

This example illustrates the augmentation of sodium hydroxide-based hair straightening on hair by an improved composition containing 1 weight percent cysteine as the auxiliary hair straightening agent. Augmentation was determined by the intermittent modulus technique described above while the hair was undergoing a straightening procedure as described below.

A hair straightening composition of this invention was prepared in the following manner. One part by weight of cysteine, in free base crystalline form, was mixed directly with 99 parts by weight of a commercial Regular-strength sodium hydroxide-based hair-straightener cream having a pH of about 12.5 to about 13.5. The resulting Composition (Composition A) contained about 2.18 weight percent sodium hydroxide and about 1 weight percent cysteine. The composition remained substantially odor-free, i.e., no sulfurous odor was detected, and was homogeneous.

The augmenting effect of the cysteine during the hair-straightening procedure was determined by intermittent modulus technique, using a fiber of natural brown-color intact hair (R. Weintraub, New York, N.Y.) of gauge length about 1.5 centimeters (about 0.6 inches) mounted between vinyl tabs. A sufficient amount of Composition A was applied to coat the fiber and was left on the hair to the point where maximum elongation of the fiber was recorded. Thereafter, the hair-straightener was rinsed from the hair with tap water.

Throughout the hair-straightening procedure, the fiber was under a constant load of 0.5 grams with an additional intermittent load of 0.5 grams applied at 30-second intervals. The chemical action of the composition on hair keratin was determined by observing changes in hair fiber integrity reflected in strength, elongation and supercontraction of the fiber undergoing the hair-straightening procedure. These changes were recorded on a Heath strip chart recorder having a 10 millivolt sensitivity using a chart speed of 0.1 inches (0.25 centimeters) per minute. A 30 millimeter (1.2 inch) pen excursion for this length fiber was equivalent to a 1 percent change in fiber length.

For example, as the strength of the fiber weakened and supercontracted during the hair-straightening treatment, the vertical excursion and starting position of the pen on the chart sharply and continuously changed. Thus, changes attributable to starting and stopping of chemical action were determined by observing reversals in these patterns, based on proportional changes in the recorder pen excursion and pen position. As a control comparison, the same hair-straightening procedure was carried out using the same commercial Regular-strength hair-straightening product (Composition CR) containing about 2.22 weight percent sodium hydroxide as supplied by the manufacturer.

The results showed that the extent and speed of the chemical action of the Regular-strength sodium hydroxide-based hair-straightener clearly was enhanced by cysteine. After Composition A was applied to the hair, faster and greater elongation of the fiber was observed than with Composition CR. Normally, from this and our prior experience, this type of increased elongation corresponds to straightening of the hair. Thus cysteine, in effect, approximately doubled the extent of change in fiber length showing greater straightening.

Another benefit observed was that chemical action substantially stopped when Composition A was removed by rinsing the fiber with water. While water rinsing is known to effect some straightening of sodium hydroxide straightened hair by reversing supercontraction, experience shows that some post-rinsing supercontraction continues owing to residual alkali in the hair.

In the case of Composition A, the observed pattern for both the rinse and post-rinse curve following rinsing removal of Composition A remained substantially uniform with substantially no post-rinse change in vertical pen position This rinse and post-rinse pattern thereby showed that chemical action on the hair had substantially stopped since further changes in supercontraction were no longer evidenced. In addition, this pattern showed that the cysteine base augmented the action of the sodium hydroxide on the hair without contributing to increased hair damage from residual sulfhydryl in the hair. On the other hand, a less uniform and typically changing pattern was observed in the vertical pen position during the rinsing and post-rinsing stage for Composition CR, as expected.

EXAMPLE 2

This example illustrates the benefits in augmenting the hair-straightening effect of sodium hydroxide-based hair-straightening compositions with 0.5 weight percent cysteine base.

The procedure of Example 1 was repeated, except that 0.5 parts by weight cysteine base was mixed into 99.5 parts by weight of the commercial Regular-strength hair-straightening composition to provide Composition B. Thus, Composition B contained about 2.21 weight percent sodium hydroxide and 0.5 weight percent cysteine base. The intermittent modulus results obtained with Composition B were again compared against those obtained with a second fiber treated with the Composition CR from Example 1.

Except for a very slightly more gradual initial pattern than was observed with 1 weight percent cysteine in Example 1, Composition B containing 0.5 weight percent cysteine also rapidly enhanced the action of the sodium hydroxide. Greater elongation of the fiber was again observed from Composition B over that observed with Composition CR. The extent of change in fiber length with Composition B was substantially similar to that of Composition A in Example 1.

Again, the restorative effect of water rinsing and post-rinse pattern showed that chemical action affecting supercontraction had substantially ceased. The overall strength of the fiber reflected in the pattern of extension of the fiber at the end of the procedure was about equivalent to that observed with 1 weight percent cysteine in Example 1.

Thus, the results of this intermittent modulus technique suggested that even at 0.5 weight percent cysteine base so augments the action of sodium hydroxide that the concentration of sodium hydroxide can be desirably and considerably decreased without sacrificing hair-straightening benefits. By lowering the concentration of sodium hydroxide, increased benefits in hair condition are gained.

EXAMPLE 3

This example illustrates the benefit of augmenting the effect of sodium hydroxide in sodium hydroxide-based hair-straighteners with cysteine base as an auxiliary hair-straightening agent at a pH of between about 12 and about 14. Results were determined by tensile wet break strength using a commercial Scott Tensile Tester (GCA/Precision Scientific, Chicago, Ill).

For this study, an aqueous solution of cysteine base at about 10 weight percent was prepared, identified as Composition D. A series of three hair-straightening cream compositions (E, F and G) were then prepared each having a sodium hydroxide concentration of about 2.0, 2.11 and 2.25 weight percent, respectively, and containing 0.5 weight percent cysteine. This was accomplished by mixing 5 parts by weight of Composition D with 95 parts by weight of a commercial sodium hydroxide-based hair-straightening cream identified as either Mild-strength to form Composition E, Regular-strength to form Composition F or Super-strength to form Composition G. For comparison, 95 parts by weight of each of the foregoing corresponding commercial hair-straightening creams, as supplied, were similarly mixed with 5 parts by weight of water to form counterpart controls, Mild-strength Composition E-1, Regular-strength Composition F-1 and Super Strength Composition G-1 having the foregoing corresponding sodium hydroxide alkalinity.

Caucasian hair was treated with the foregoing hair-straightener creams using 5-inch tresses of natural dark brown hair (DeMeo Brothers, New York, N.Y.), each tress being about 2 grams in weight. About 5 grams of one of the above hair-straighteners was applied to one of the tresses, generally following the manufacturer's instructions to simulate actual on-head procedures. After about 18 minutes, the hair straightener was removed by thoroughly rinsing the hair tress using warm tap water, and was then given two latherings with the acidic neutralizing shampoo supplied with the commercial product. This same procedure was followed using Compositions E-G and E-1 - G-1.

The tensile wet elongation and break strength of the straightened hair was determined by removing 25 fibers from the tress after the procedure. The fibers were equilibrated in water overnight. The gram force required to break the wet fiber under elongation while submerged in water was measured using the Scott Tensile Tester and the mean break force was determined. For comparison, the tensile wet elongation and break strength of fibers from an untreated tress was similarly measured. The results are compared in the following Table.

| Hair-Straightener Composition | Mean Break Force (Grams) | % Loss in Strength | % Diff. (Note 1) |
|---|---|---|---|
| None (control) | 40.62 | — | — |
| E | 29.36 | 27.7 | +0.5 |
| E-1 | 29.17 | 28.2 | |
| F | 31.23 | 23.1 | +2.1 |
| F-1 | 30.38 | 25.2 | |
| G | 27.21 | 33.0 | +1.9 |
| G-1 | 26.43 | 34.9 | |

(Note 1) % Differential was calculated from the loss in strength obtained with the corresponding commercial composition commercial composition containing no cysteine in each pair.

These results also confirmed the utility of a cysteine as an auxiliary hair-straightening agent in augmenting and enhancing the hair-straightening benefit of sodium hydroxide hair straightener. Based on the mean break-force data, differences between individual results were not statistically different at 99 percent level of confidence. The data suggest, therefore, that the auxiliary hair-straightening agent exerted its chemical action without increasing hair damage.

Indeed, the data for loss in hair strength and the differential between paired data show that, in all cases where cysteine was used, a benefit in decreased loss of hair strength was measured.

Further, this example illustrates the utility of cysteine as a component in a two-package hair-straightening system where the cysteine is contained as a powder in one of the packages and the sodium hydroxide is contained in an aqueous cream in a second package, so that a hair-straightener is formed when the components of the two packages are mixed.

EXAMPLE 4

This example illustrates that the same beneficial effects obtained with cysteine in Example 3 were not obtained with ammonium thioglycolate, the hair keratin-disulfide reducing agent commonly used in conventional cold-waving practice.

The procedure of Example 3 was followed except that ammonium thioglycolate was added at 0.5 weight percent to only the Regular-strength commercial sodium hydroxide-based cream to form Composition H. Composition H was prepared by mixing 0.72 parts by weight of aqueous 70 percent ammonium thioglycolate with 99.28 parts by weight Regular-strength commercial product. For comparison, the Regular-Strength commercial cream was similarly mixed with water and identified as Composition H-1. The tensile data are shown below.

| Hair-Straightener Composition | Mean Break Force (Grams) | % Loss in Strength | % Diff. * |
|---|---|---|---|
| None (control) | 35.70 | — | — |
| H | 25.22 | 29.4 | −1.4 |
| H-1 | 25.70 | 28.0 | |

*See Note 1, Example 3.

These data show that the addition of ammonium thioglycolate, albeit in a relatively small amount of 0.5 weight percent, resulted in an undesirable increased loss of hair strength.

EXAMPLE 5

This example illustrates the beneficial hair-straightening effect of an improved no-base sodium hydroxide-based hair-straightening system of this invention using a hair-straightener comprising a mixture of about 2.2 weight percent sodium hydroxide and about 0.75 weight percent cysteine.

For this study, 3.3 grams of cysteine base in substantially powder form were mixed with 430 grams of commercial Regular-strength sodium hydroxide-based hair straightener cream containing about 2.22 weight percent sodium hydroxide. The resulting improved hair-straightener was identified as Composition I. The effectiveness of the improved hair-straightener was evaluated by professional beauticians in a half-head comparison test under professional salon conditions. Five volunteers (A-E) each received a straightening procedure with the Composition I on one side of the head, with the remaining opposite side receiving a similar straightening procedure with commercial Super-strength sodium hydroxide-based hair straightener cream (Composition CS) containing about 2.4 weight percent sodium hydroxide.

In all cases, the straightener products were applied to virgin curly new growth portions of the hair in the conventional manner employed for no-base hair relaxers following the manufacturer's instructions. For patrons having hair characterized as fine, medium and coarse, the respective total contact time with the hair-straightening composition was adjusted as needed. This usually corresponds to about 13 minutes, about 15 minutes and about 18 minutes for fine, medium and coarse hair respectively.

Prior to receiving the straightening procedure, hair fibers were removed from each volunteer. When the desired amount of straightening was obtained, the hair was rinsed thoroughly with water until substantially all visible traces of the straightener product were removed from the hair and scalp. At this stage, sufficient hair fibers were again removed from each side of the patron's hair for tensile evaluation on the Scott Tensile Tester. The procedure was then completed by shampooing the entire head of hair with the acidic neutralizer shampoo supplied by the manufacturer in the usual manner.

The results are compared in the following Table.

| Volunteer | Mean Breakforce in Grams* | | | % Loss in Fiber Strength | |
|---|---|---|---|---|---|
| | (a) Control | (b) Comp. CS | (c) Comp. I | (d) Comp. CS | (e) Comp. I |
| A | 19.77 | 16.47 | 14.75 | −16.6 | −25.4 |
| B | 19.47 | 15.76 | 17.47 | −19.1 | −10.2 |
| C | 17.91 | 16.94 | 15.81 | −5.4 | −11.7 |
| D | 11.89 | 10.37 | 11.55 | −12.8 | −2.8 |
| E | 23.77 | 18.57 | 19.52 | −21.8 | −17.8 |
| Composite % loss of strength for A-E | | | | −15.2 | −13.6 |
| Standard Deviation: | | | | 5.71 | 7.58 |

*Column (a) is the data for the control fibers sampled prior to the hair-straightening procedure; Column (b) is the data obtained for the side straightened with commercial Super-strength cream (Composition CS); and Column (c) is the data obtained for the side straightened with improved Composition I.
**Column (d) is the calculated data for percent loss in fiber strength from the use of Composition CS; and Column (e) is the calculated data for percent loss in fiber strength from the use of Composition I.

The overall composite data on percent loss in fiber strength showed a beneficial advantage for Composition I over the corresponding commercial Super-strength hair-straightener Composition CS. The difference between the individual mean breakforce data for each volunteer were not statistically significant at a 99 percent level of confidence. However, the individual data show that in 3 of 5 instances (60 percent of the population) the chemical action of Composition I containing a lower amount of sodium hydroxide showed a beneficial advantage.

The straightening effect obtained with Composition I showed that the improved Regular-strength sodium hydroxide cream was enhanced to a level approaching that of the Super-strength cream. On one person's hair, the level of straightening observed within about 13 minutes with Composition I was equivalent to that observed at 18 minutes with the commercial Super-strength composition. While the overall level of straightening observed was relatively lower than that obtained with the commercial Super-strength product, the overall straightening effect of Composition I was considered excellent and was preferred on three of the five volunteers.

EXAMPLE 6

The procedure of Example 5 was followed, except that 0.5 weight percent cysteine base was mixed with the commercial Regular-strength commercial sodium hydroxide-based hair straightener cream. The resulting improved hair-straightener, Composition J, contained about 2.2 weight percent sodium hydroxide. Composition J was used to straighten the hair of five volunteers (F-J) having coarse afro-style hair in a half-head procedure. For comparison, the commercial Super-strength cream of Example 5 was used. In addition, for this study, the color of the volunteers' hair was observed for discoloration of white (grey) fibers.

Composition J produced good straightening or relaxation of the hair, a soft feel to the hair and brightened the hair color. The hair-straightening obtained with the improved Composition J was judged equivalent (rated good to excellent) on four of the five volunteers (80 percent of the population). On the one remaining volunteer, the straightening effects were relatively low (rating of less than good) with either compositions indicating this person's hair was particularly resistant to straightening generally. None of the volunteers experienced scalp irritation.

Four of the five volunteers had some grey fibers, including the volunteer receiving the relatively low-level of straightening. On all these volunteers, the grey fibers were brightened on the side straightened by Composition J, whereas the grey fibers were yellowed on the side straightened with the commercial Super-strength cream.

The present invention has been described generally and with respect to preferred embodiments. It will be understood that modifications and variations of the disclosed method and compositions may be made without departing from the spirit and scope of the novel concept of the present invention.

What is claimed is:

1. An improved aqueous hair-straightening composition having a pH of between about 12 and about 14 comprising in dissolved admixture at least two active hair-straightening agents, said composition comprising about 1 to about 2.5 weight percent on a total composition weight basis of an alkali metal hydroxide selected from the group consisting of sodium hydroxide, potassium hydroxide and lithium hydroxide as a main hair-straightening agent and a less amount of an auxiliary hair-straightening agent that is a hair keratin-disulfide reducing agent having a sulfhydryl functional group available and is selected from the group consisting of cysteine, water-soluble homologs of cysteine, and water-soluble derivatives of cysteine having none, one or both of the polar amino and carboxy acid groups thereof substituted, said auxiliary agent being in a free base form or in a mineral acid salt form thereof.

2. The hair-straightening composition of claim 1 wherein the alkali metal hydroxide is sodium hydroxide.

3. The hair-straightening composition of claim 1 wherein the hair keratin-disulfide reducing agent comprises about 0.1 to about 1.5 weight percent of the total weight of the composition.

4. The hair-straightening composition of claim 1 wherein the hair keratin-disulfide reducing agent is selected from the group consisting of cysteine, N-substituted derivatives of cysteine, lower alkyl esters of cysteine having up to about three carbon atoms in the alkyl group, homocysteine, homocysteine thiolactone and N-substituted derivatives of homocysteine thiolactone alone or in admixture.

5. The hair-straightening composition of claim 1 wherein the hair keratin-disulfide reducing agent is cysteine.

6. The hair-straightening composition of claim 2 wherein the sodium hydroxide comprises about 1.5 to about 2.25 weight percent and the hair keratin-disulfide reducing agent comprises about 0.25 to about 1.0 weight percent of the total weight of the composition.

7. The hair-straightening composition of claim 6 wherein the hair keratin-disulfide reducing agent is cysteine.

8. The hair-straightening composition of claim 1 wherein the auxiliary hair-straightening agent is cysteine hydrochloride.

9. In a method of straightening hair with a no-base aqueous hair-straightening composition in which the hair-straightening composition is applied to the hair and the hair is physically smoothed, rinsed, shampooed, set and dried, the improvement which comprises using as the active hair-straightener the composition of claim 1.

10. In an improved no-base aqueous hair-straightening composition having a pH of between about 12 and about 14 and containing an effective amount of sodium hydroxide as the active hair straightening agent, the improvement comprising the inclusion of about 0.1 to about 1.5 weight percent on a total composition weight basis of an auxiliary hair-straightening agent that is a hair keratin-disulfide reducing agent having a sulfhydryl functional group available and is selected from the group consisting of cysteine, water-soluble homologs of cysteine, and water-soluble derivatives of cysteine having none, one or both of the polar amino and carboxy acid groups thereof substituted, said auxiliary agent being in a free base form or in a mineral acid salt form thereof, the amount of said auxiliary hair-straightening agent being less than the amount of sodium hydroxide.

11. The hair-straightening composition of claim 10 wherein the auxiliary hair-straightening agent is selected derivatives of cysteine, lower alkyl esters of cysteine having up to about three carbon atoms in the alkyl group, homocysteine, homocysteine thiolactone and N-substituted derivatives of homocysteine thiolactone alone or in admixture.

12. The hair-straightening composition of claim 10 wherein the auxiliary hair-straightening agent is cysteine.

13. The hair-straightening composition of claim 12 wherein sodium hydroxide comprises about 1 to about 2.5 weight percent of the total weight of the composition.

14. The hair-straightening composition of claim 12 wherein the cysteine is incorporated in the form of cysteine hydrochloride.

15. A no-base aqueous hair-straightening composition having a pH of between about 12 and about 13.5 comprising, as the active hair-straightening agent, a mixture of about 1.5 to 2.2 weight percent sodium hydroxide and about 0.25 to about 1 weight percent cysteine, based on the total weight of the composition.

16. The hair-straightening composition of claim 15 wherein the cysteine is incorporated in the form of cysteine hydrochloride.

17. In a method of straightening hair with a no-base aqueous hair-straightening composition in which the hair-straightening composition is applied to the hair and the hair is physically smoothed, rinsed, shampooed, set and dried, the improvement which comprises using as the active hair-straightener the composition of claim 13.

18. An improved no-base hair-straightening system in at least two packages comprising:

(a) a first package comprising an aqueous composition having a pH between about 12 and about 14 containing, as a hair-straightening agent, sodium hydroxide which comprises between about 1 and about 2.5 weight percent based on the total weight of a hair-straightener to be applied to the hair; and (b) a second package including an auxiliary hair-straightening agent comprising a hair keratin-disulfide reducing agent having a sulfhydryl functional group available from the sulfur-containing amino acid cysteine, water-soluble homologs of cysteine and water-soluble derivatives of cysteine having none, one or both of the polar amino and carboxy acid groups substituted present in a free base form or as a mineral acid salt thereof in an amount sufficient to form the hair-straightener when the contents of the second package are admixed with the contents of the first package, the amount of auxiliary hair-straightening agent being less than the amount of sodium hydroxide in the admixture.

19. The hair-straightening system of claim 18 wherein the auxiliary hair-straightening agent comprises about 0.1 to about 1.5 weight percent based on the total weight of the admixture.

20. The hair-straightening system of claim 18 wherein the sodium hydroxide in the first package comprises about 1.5 to about 2.2 weight percent and the auxiliary hair-straightening agent comprises about 0.25 to about 1 weight percent based on the total weight of the hair-straightener.

21. In a method of straightening hair with a no-base aqueous hair-straightening composition in which the hair-straightening composition is applied to the hair and the is hair physically smoothed, rinsed, shampooed, set and dried, the improvement which comprises using as the active hair-straightener the composition obtained with the hair-straightening system of claim 14.

22. The hair-straightening system of claim 18 wherein the auxiliary hair-straightening agent is cysteine.

23. The system of claim 22 wherein the cysteine is incorporated in the form of cysteine hydrochloride.

24. The hair-straightening system of claim 14 wherein the contents of the first package are in an emulsion cream form before being admixed with the contents of the second package.

25. The hair-straightening system of claim 24 wherein the contents of the second package are in a substantially dry powder form before being admixed with the contents of the first package.

26. The hair-straightening system of claim 24 wherein the contents of the second package are in an aqueous liquid form before being admixed with the contents of the first package.

27. The hair-straightening system of claim 20 wherein the contents of the second package include cosmetic adjuvants.

* * * * *

UNITED STATES PATENT AND TRADEMARK OFFICE
CERTIFICATE OF CORRECTION

PATENT NO. : 4,992,267

DATED : February 12, 1991

INVENTOR(S) : Marion DenBeste and Muhammad Akhtar

It is certified that error appears in the above-identified patent and that said Letters Patent is hereby corrected as shown below:

Col. 17, line 20 (in Claim 1) change "less" to "lesser".

Col. 18, line 14 (in Claim 11) before the word "derivatives" insert "from the group consisting of cysteine, N-substituted".

Col. 18, line 31 (in Claim 15) change "12" to "12.5".

Col. 18, line 44 (in Claim 17) change "13" to "15".

Col. 19, line 16 (in Claim 21) change "14" to "18".

Col. 20, line 3 (in Claim 24) change "14" to "18".

Col. 20, line 15 (in Claim 27) change "20" to "26".

Signed and Sealed this

Twenty-seventh Day of April, 1993

Attest:

MICHAEL K. KIRK

*Attesting Officer*    *Acting Commissioner of Patents and Trademarks*